(12) United States Patent
Hershey et al.

(10) Patent No.: US 11,957,911 B2
(45) Date of Patent: Apr. 16, 2024

(54) NEUROMODULATION FOR NEUROINFLAMMATION TREATMENTS WITH PARAMETERS CONTROLLED USING BIOMARKERS

(71) Applicant: Boston Scientific Neuromodulation Corporation, Valencia, CA (US)

(72) Inventors: Bradley Lawrence Hershey, Carrollton, TX (US); Changfang Zhu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 433 days.

(21) Appl. No.: 17/330,756

(22) Filed: May 26, 2021

(65) Prior Publication Data

US 2021/0275818 A1    Sep. 9, 2021

Related U.S. Application Data

(63) Continuation of application No. 16/360,321, filed on Mar. 21, 2019, now Pat. No. 11,040,204, which is a
(Continued)

(51) Int. Cl.
*A61N 1/36* (2006.01)
*A61M 5/172* (2006.01)
(Continued)

(52) U.S. Cl.
CPC ....... *A61N 1/36139* (2013.01); *A61M 5/1723* (2013.01); *A61N 1/36103* (2013.01);
(Continued)

(58) Field of Classification Search
CPC ............ A61N 1/36139; A61N 1/36103; A61N 2/002; A61N 2/006; A61N 5/0622;
(Continued)

(56) References Cited

U.S. PATENT DOCUMENTS

2005/0125044 A1   6/2005 Tracey
2010/0217172 A1   8/2010 Hyde et al.
(Continued)

OTHER PUBLICATIONS

U.S. Appl. No. 15/346,258, filed Nov. 8, 2016, Neuromodulation for Neuroinflammation Treatments With Parameters Controlled Using Biomarkers.
(Continued)

*Primary Examiner* — Erin M Piateski
(74) *Attorney, Agent, or Firm* — Schwegman Lundberg Woessner, P.A.

(57) ABSTRACT

An example of a system for modulating neuroinflammation at a tissue site in a patient includes a neuromodulation output circuit, a memory, and a control circuit. The neuromodulation output circuit may be configured to deliver the neuromodulation. The memory may be configured to store a neuromodulation parameter set selected to modulate neural activity at the tissue site and a sensed biomarker parameter. The biomarker parameter may include a measure of a biomarker or a measure of a derivative of the biomarker. The biomarker may be indicative of the neuroinflammation at the tissue site. The control circuit may be configured to control the delivery of the neuromodulation using the neuromodulation parameter set and adjust one or more parameters of the neuromodulation parameter set using the biomarker parameter.

20 Claims, 5 Drawing Sheets

Related U.S. Application Data continuation of application No. 15/346,258, filed on Nov. 8, 2016, now abandoned.

(60) Provisional application No. 62/257,457, filed on Nov. 19, 2015.

(51) Int. Cl.
*A61N 2/00* (2006.01)
*A61N 5/06* (2006.01)
*A61M 5/14* (2006.01)

(52) U.S. Cl.
CPC ............ *A61N 2/002* (2013.01); *A61N 2/006* (2013.01); *A61N 5/0622* (2013.01); *A61M 5/14* (2013.01); *A61N 2005/0626* (2013.01); *A61N 2005/0659* (2013.01)

(58) Field of Classification Search
CPC ... A61N 2005/0626; A61N 2005/0659; A61M 5/1723; A61M 5/14
USPC ............................................................ 607/2
See application file for complete search history.

(56) References Cited

U.S. PATENT DOCUMENTS

| | | | |
|---|---|---|---|
| 2011/0106208 A1* | 5/2011 | Faltys | A61N 1/36071 607/46 |
| 2011/0152967 A1* | 6/2011 | Simon | A61N 1/36025 607/45 |
| 2012/0016174 A1 | 1/2012 | De et al. | |
| 2012/0238838 A1 | 9/2012 | Hyde et al. | |
| 2014/0142669 A1 | 5/2014 | Cook et al. | |
| 2014/0243714 A1 | 8/2014 | Ward et al. | |
| 2014/0301947 A1 | 10/2014 | Owen et al. | |
| 2014/0330349 A1* | 11/2014 | Levine | A61N 1/36175 607/72 |
| 2017/0079598 A1* | 3/2017 | Stolen | A61B 5/0215 |
| 2017/0143972 A1 | 5/2017 | Hershey et al. | |
| 2018/0267015 A1* | 9/2018 | Meyer | G01N 33/49 |
| 2019/0217100 A1 | 7/2019 | Hershey et al. | |
| 2020/0246617 A1* | 8/2020 | Errico | A61N 1/3603 |

OTHER PUBLICATIONS

U.S. Appl. No. 16/360,321, filed Mar. 21, 2019, Neuromodulation for Neuroinflammation Treatments With Parameters Controlled Using Biomarkers.
"U.S. Appl. No. 15/346,258, Advisory Action dated Feb. 28, 2019", 4 pgs.
"U.S. Appl. No. 15/346,258, Final Office Action dated Dec. 21, 2018", 15 pgs.
"U.S. Appl. No. 15/346,258, Non Final Office Action dated Jun. 12, 2018", 15 pgs.
"U.S. Appl. No. 15/346,258, Response filed Sep. 11, 2018 to Non Final Office Action dated Jun. 12, 2018", 9 pgs.
"U.S. Appl. No. 15/346,258, Response filed Feb. 11, 2019 to Final Office Action dated Dec. 21, 2018", 9 pgs.
"U.S. Appl. No. 16/360,321, 3.12 Amendment filed May 14, 2021", 6 pgs.
"U.S. Appl. No. 16/360,321, Non Final Office Action dated Nov. 10, 2020", 12 pgs.
"U.S. Appl. No. 16/360,321, Notice of Allowance dated Feb. 18, 2021", 7 pgs.
"U.S. Appl. No. 16/360,321, Preliminary Amendment filed Apr. 9, 2019", 6 pgs.
"U.S. Appl. No. 16/360,321, PTO Response to Rule 312 Communication dated May 24, 2021", 2 pgs.
"U.S. Appl. No. 16/360,321, Response filed Jan. 28, 2021 to Non Final Office Action dated Nov. 10, 2020", 10 pgs.

* cited by examiner

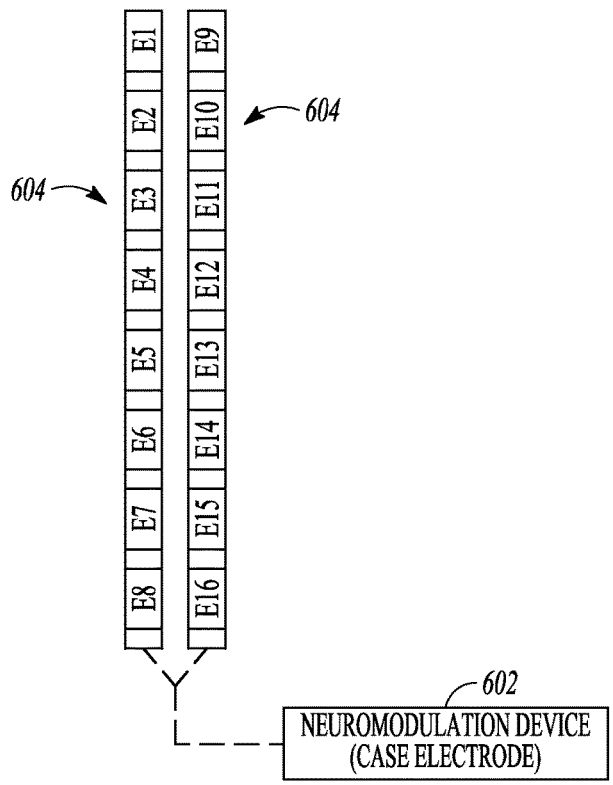
FIG. 6
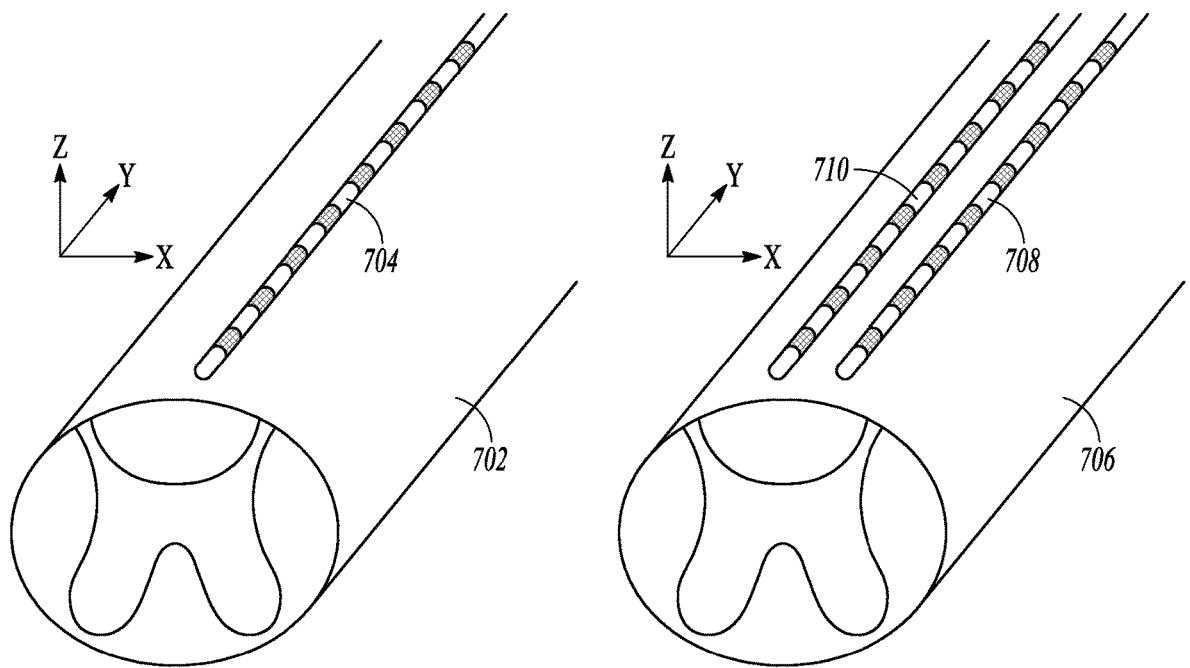
FIG. 7A  FIG. 7B

NEUROMODULATION FOR NEUROINFLAMMATION TREATMENTS WITH PARAMETERS CONTROLLED USING BIOMARKERS

CLAIM OF PRIORITY

This application is a continuation of U.S. application Ser. No. 16/360,321, filed Mar. 21, 2019, which is a continuation of U.S. application Ser. No. 15/346,258, filed Nov. 8, 2016, which claims the benefit of priority under 35 U.S.C. § 119(e) of U.S. Provisional Patent Application Ser. No. 62/257,457, filed on Nov. 19, 2015, all of which are herein incorporated by reference in their entireties.

TECHNICAL FIELD

This document relates generally to medical systems, and more particularly, to systems and methods for delivering neuromodulation to treat neuroinflammation and controlling the delivery of the neuromodulation using sensed biomarkers.

BACKGROUND

Neuromodulation, also referred to as neurostimulation, has been proposed as a therapy for a number of conditions. Examples of neuromodulation include Spinal Cord Stimulation (SCS), Deep Brain Stimulation (DBS), Peripheral Nerve Stimulation (PNS), and Functional Electrical Stimulation (FES). Implantable neuromodulation systems have been applied to deliver such a therapy. An implantable neuromodulation system may include an implantable neurostimulator, also referred to as an implantable pulse generator (IPG), and one or more implantable leads each including one or more electrodes. The implantable neurostimulator delivers neuromodulation energy through one or more electrodes placed on or near a target site in the nervous system. An external programming device is used to program the implantable neurostimulator with stimulation parameters controlling the delivery of the neuromodulation energy.

Neuromodulation energy may be delivered in any form of energy that is capable of modulating characteristics of nervous tissue and/or electrical activities in the nervous system by stimulating target sites in the nervous system. The delivery may be controlled using stimulation parameters that specify spatial (where to stimulate), temporal (when to stimulate), and informational (patterns of pulses directing the nervous system to respond as desired) aspects of a pattern of neuromodulation pulses. Recent research has shown new schemes for setting and adjusting such parameters to expand the indications for neuromodulation as well as to improve efficacy of neuromodulation therapies.

SUMMARY

An example (e.g., "Example 1") of a system for modulating neuroinflammation at a tissue site in a patient includes a neuromodulation output circuit, a memory, and a control circuit. The neuromodulation output circuit may be configured to deliver the neuromodulation. The memory may be configured to store a neuromodulation parameter set selected to modulate neural activity at the tissue site and a sensed biomarker parameter. The biomarker parameter may include a measure of a biomarker or a measure of a derivative of the biomarker. The biomarker may be indicative of the neuroinflammation at the tissue site. The control circuit may be configured to control the delivery of the neuromodulation using the neuromodulation parameter set and adjust one or more parameters of the neuromodulation parameter set using the biomarker parameter.

In Example 2, the subject matter of Example 1 may optionally be configured such that the control circuit is configured to compare the biomarker parameter to a reference value and to adjust the neuromodulation parameter set using an outcome of the comparison.

In Example 3, the subject matter of any one or any combination of Examples 1 and 2 may optionally be configured to include an implantable neuromodulation device. The implantable neuromodulation device may include the neuromodulation output circuit, the memory, and the control circuit.

In Example 4, the subject matter of any one or any combination of Examples 1-3 may optionally be configured to further include a biomarker sensor configured to sense the biomarker parameter.

In Example 5, the subject matter of Example 4 may optionally be configured such the biomarker sensor includes an implantable biomarker sensor.

In Example 6, the subject matter of any one or any combination of Examples 4 and 5 may optionally be configured such that the biomarker sensor is configured to sense the biomarker parameter being a measure of a translocator protein concentration.

In Example 7, the subject matter of any one or any combination of Examples 4 and 5 may optionally be configured such that the biomarker sensor is configured to sense the biomarker parameter being a measure of a temporal activation of the microglial cell.

In Example 8, the subject matter of any one or any combination of Examples 4 and 5 may optionally be configured such that the biomarker sensor is configured to sense the biomarker parameter being a measure of a spatial activation of the microglial cell.

In Example 9, the subject matter of any one or any combination of Examples 4 and 5 may optionally be configured such that the biomarker sensor is configured to sense the biomarker parameter being a measure of or a cytokine concentration.

In Example 10, the subject matter of any one or any combination of Examples 4-9 may optionally be configured such that the biomarker sensor is configured to sense a biomarker parameter indicative of a degree of the neuroinflammation at the tissue site.

In Example 11, the subject matter of Example 10 may optionally be configured such that the biomarker sensor is configured to sense a biomarker parameter indicative of an intensity of pain.

In Example 12, the subject matter of any one or any combination of Examples 4-11 may optionally be configured such that the biomarker sensor is configured to sense a biomarker parameter indicative of a need for treating the neuroinflammation.

In Example 13, the subject matter of any one or any combination of Examples 4-9 may optionally be configured such that the neuromodulation output circuit is configured to deliver electrical pulses.

In Example 14, the subject matter of any one or any combination of Examples 4-9 may optionally be configured to include a neuromodulation delivery device configured to deliver stimuli including one or more of electrical stimuli, magnetic stimuli, optical stimuli, acoustic stimuli, and chemical stimuli, and that the neuromodulation output circuit is configured to deliver the neuromodulation by controlling the delivery of the stimuli from the neuromodulation delivery device.

In Example 15, the subject matter of Example 14 may optionally be configured such that the neuromodulation delivery device is configured to emit a light, and wherein the neuromodulation output circuit is configured to deliver the neuromodulation by controlling the emission of the light from the neuromodulation delivery device.

In an example (e.g., "Example 16"), a method for delivering neuromodulation to a patient is disclosed. The method may include delivering the neuromodulation; controlling the delivery of the neuromodulation using a neuromodulation parameter set selected to modulate neural activity at a tissue site; sensing a biomarker parameter, and adjusting the neuromodulation parameter set using the biomarker parameter. The biomarker parameter may be a measure of a biomarker or a measure of a derivative of the biomarker. The biomarker may be indicative of neuroinflammation at the tissue site.

In Example 17, the subject matter of Example 16 may optionally be configured such that the biomarker is indicative of activation of microglial cells in the tissue site.

In Example 18, the subject matter of adjusting the neuromodulation parameter set using the biomarker parameter as found in any one or any combination of Examples 16 and 17 may optionally include comparing the biomarker parameter to a reference value and adjusting the neuromodulation parameter set using an outcome of the comparison.

In Example 19, the subject matter of the biomarker as found in any one or any combination of Examples 16-18 may optionally include at least one of a translocator protein concentration, a temporal activation of the microglial cell, a spatial activation of the microglial cell, or a cytokine concentration.

In Example 20, the subject matter of delivering the neuromodulation as found in any one or any combination of Examples 16-19 may optionally include delivering electrical pulses.

In Example 21, the subject matter of delivering the neuromodulation as found in any one or any combination of Examples 16-20 may optionally include emitting a light.

In Example 22, the subject matter of delivering the neuromodulation as found in any one or any combination of Examples 16-21 may optionally include delivering the neuromodulation to at least one of a dorsal column, a thalamus, a cortex, a peripheral nerve, a vagus nerve, a dorsal root ganglion, a dorsal longitudinal fasciculus, or a dorsal horn.

In Example 23, the subject matter of delivering the neuromodulation as found in any one or any combination of Examples 16-21 may optionally include delivering the neuromodulation to the tissue site.

In Example 24, the subject matter of delivering the neuromodulation as found in any one or any combination of Examples 16-21 may optionally include delivering the neuromodulation to an upstream or downstream pathway relative to the tissue site.

In Example 25, the subject matter of delivering the neuromodulation as found in any one or any combination of Examples 16-21 may optionally include delivering the neuromodulation to a nerve that modulates the neuroinflammation systemically.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various examples are illustrated by way of example in the figures of the accompanying drawings. Such examples are demonstrative and not intended to be exhaustive or exclusive examples of the present subject matter.

FIG. 6 illustrates an example of some features of the neuromodulation leads and a pulse generator.

FIG. 7A illustrates a schematic view of an example of a single neuromodulation lead implanted over approximately the longitudinal midline of the patient's spinal cord.

FIG. 7B illustrates a schematic view of an example of an neuromodulation lead that has been implanted more laterally with respect to the spinal cord, thereby placing it proximate the dorsal horn of the spinal cord, and the other neuromodulation lead that has been implanted more medially with respect to the spinal cord, thereby placing it proximate the dorsal column of the spinal cord.

DETAILED DESCRIPTION

Figure 1:
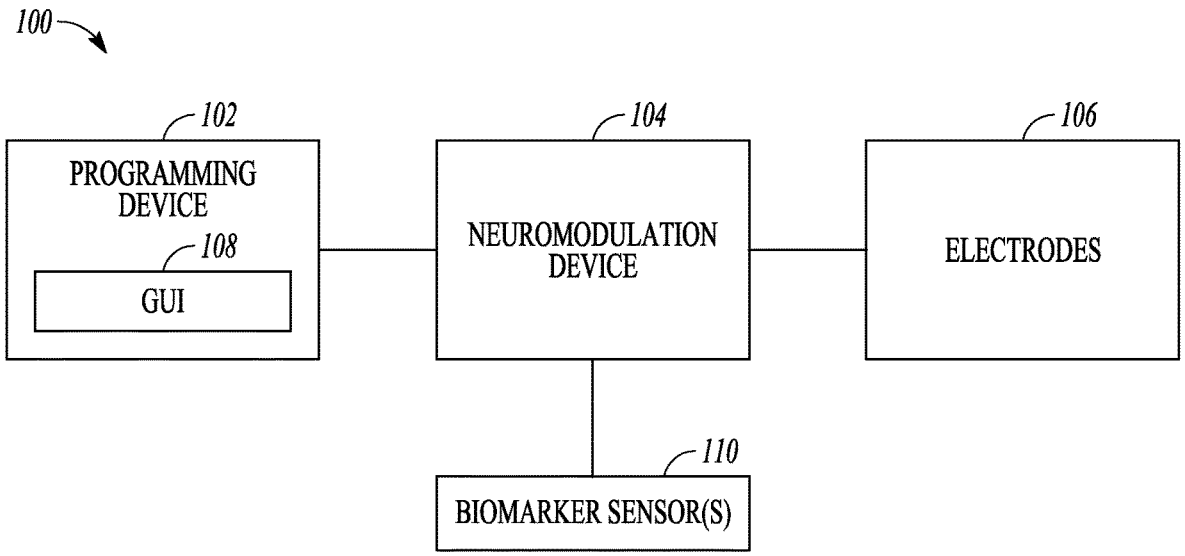
FIG. 1 illustrates an example of a neuromodulation system.

In the following detailed description, reference is made to the accompanying drawings which form a part hereof, and in which is shown by way of illustration specific examples in which the invention may be practiced. These examples are described in sufficient detail to enable those skilled in the art to practice the invention, and it is to be understood that the examples may be combined, or that other examples may be utilized and that structural, logical and electrical changes may be made without departing from the spirit and scope of the present invention. References to "an", "one", or "various" examples in this disclosure are not necessarily to the same example, and such references contemplate more than one example. The following detailed description provides examples, and the scope of the present invention is defined by the appended claims and their legal equivalents.

This document discusses, among other things, a system for treating neuroinflammation in a patient by delivering neuromodulation to a tissue site in a patient. Neuroinflammation can be inflammation of nervous tissue in the tissue site. The tissue site can include portions of, for example, dorsal column, thalamus, cortex, peripheral nerve, dorsal root ganglion, dorsal longitudinal fasciculus, dorsal horn, or periaqueductal grey (PAG). The tissue site can include other targets, such as those that modulate inflammation systemically (e.g., a vagus nerve). By way of example, neuromodulation can be used to modulate neuroinflammation, such as by reducing or increasing microglial cell activation in the tissue site. Such neuromodulation can be used to treat, for example, chronic pain, Alzheimer's disease, unipolar depression, bipolar depression, multiple sclerosis, rheumatoid arthritis, or irritable bowel disease.

Microglia can have metabotropic glu receptors (mGluRs) that allow the microglia to respond to excitatory neuronal signals. Because mGluRs can modify microglia phenotype, patterns of activation of glutamanergic neurons may modulate neuroinflammation. A biomarker can be used as a measure in the patient, which is indicative of a phenomenon, such as the above mentioned pathologies. A biomarker of the tissue site can include translocator protein (TSPO). A measure of TSPO, such as concentration of TSPO, can be indicative of microglial cell activation. Research has shown that TSPO may be inversely correlated to chronic pain intensity. The measure of TSPO can be used to classify patients as having, for example, normal or chronic pain. Cerebrospinal fluid (CSF) levels of TSPO can be detected using an implantable sensor system to determine a surrogate measure of pain intensity. In an example, TSPO levels at a tissue site can be detected using an implantable sensor system, and the detected level of TSPO at the tissue site can be used a surrogate for pain intensity of the patient. In one example, a signal corresponding to TSPO levels at the tissue site can be used to screen a patient to determine whether the patient would be a candidate for device implantation.

The present system delivers neuromodulation for modulating neural activities at the tissue site of the patient. The system can deliver the neuromodulation and sense the biomarker in the surrounding environment for indicating the patient's response to the delivery of the neuromodulation. The system can store patient data, such as a biomarker parameter associated with the tissue site, and can compare the biomarker parameter to a reference value. Based on the comparison, the system can adjust a parameter set controlling the delivery of the neuromodulation. As used in this document, a "biomarker parameter" can include a measure of the biomarker and/or a measure of a derivative of the biomarker. In various examples, one or more biomarker parameters each being a measure of the biomarker or a measure of a derivative of the biomarker can be sensed.

Disclosed herein include systems, devices, and methods for optimizing treatments for a patient. Metrics that quantify neuroinflammation can be used to determine optimal stimulation targets and parameters for the neuromodulation (e.g., temporal and spatial parameters in a parameter set), and to ensure therapy longevity. Examples of a biomarker can include a neuroinflammatory measure that quantifies microglial activation at a tissue site; cytokine concentration in the cerebrospinal fluid (CSF), dorsal horn, brain ventricles, or brain tissue; or translocator protein (TSPO) levels in the dorsal horn, CSF, brain, ventricles, dorsal root ganglion (DRG). One application of the present subject matter can include determining patient-specific treatment approaches to meet a desired therapeutic goal.

In various examples, neuromodulation as discussed in this document may use electrical, magnetic, optical, acoustic, chemical, pharmacological, and/or any other forms of energy or modality to modulate neural activities. While a system for neuromodulation using electrical pulses and/or light is specifically discussed as examples in this document, the present subject matter can be applied in neuromodulation using any form of energy that is known to be capable of modulating neural activities and/or nervous tissue properties.

FIG. 1 illustrates an example of a neuromodulation system 100. The illustrated system 100 includes a programming device 102, a neuromodulation device 104, electrodes 106, and one or more biomarker sensors 110. The neuromodulation device 104 can be an external device operable external to the patient or an implantable device placed within the patient. The neuromodulation device 104 is configured to be electrically connected to the electrodes 106 and deliver neuromodulation energy, such as in the form of electrical pulses, to the tissue site through the electrodes 106. In one example, the neuromodulation device 104 is configured to deliver neuromodulation energy in the form of light, such as using an optical stimulator (e.g., an optical emitter or an optical modulator). The delivery of the neuromodulation is controlled using a neuromodulation parameter set. The neuromodulation parameter set can include one or more neuromodulation parameters, such as a neuromodulation parameter specifying an aspect of the electrical pulses or a selection of electrodes through which each of the electrical pulses is delivered.

The neuromodulation parameters (also referred to as "the parameters") can define a neuromodulation pattern (or waveform of stimuli), such as a stochastic pattern, a burst pattern, a frequency modulated pattern, a pulse width modulated pattern, an amplitude modulated pattern, or a biomimetic pattern. In an example, a biomimetic pattern includes a combination of two or more patterns, such as a stochastic pattern and a rate modulated pattern. In one example, the neuromodulation pattern can be a dynamic pattern that can change over time, such as in response to changing results of measurement of a biomarker of the tissue site.

In various examples, at least some parameters of the neuromodulation parameter set are user-programmable parameters that are controllable by a user, such as a physician or other caregiver. The programming device 102 can provide the user with accessibility to the user-programmable parameters. In various examples, the programming device 102 is configured to be communicatively coupled to the neuromodulation device 104 via a wired or wireless link. In the illustrated example, the programming device 102 includes a graphical user interface (GUI) 108 that allows the user to set or adjust values of the user-programmable neuromodulation parameters.

The one or more biomarker sensors 110 can each be configured for sensing one or more biomarker parameters associated with a tissue site. The biomarker parameters can each include a measure of the biomarker or a measure of a derivative of the biomarker. In various examples, the biomarker parameter is indicative the presence and/or amount of a biomarker in the tissue site, such as a concentration of the biomarker at the tissue site. In one example, the one or more biomarker sensors 110 include one or more implantable biomarker sensors.

Figure 2:
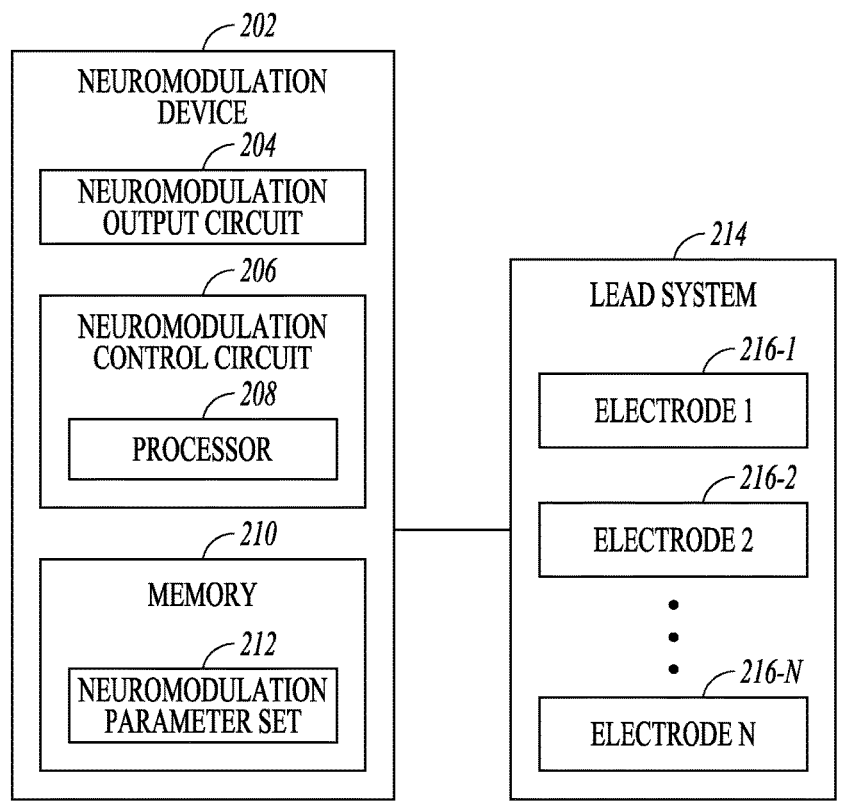
FIG. 2 illustrates an example of a neuromodulation device and a lead system of a neuromodulation system, such as the system of FIG. 1.

FIG. 2 illustrates an example of a neuromodulation device 202 connected to a lead system 214, such as can be implemented as the neuromodulation device 104 in the neuromodulation system 100. The illustrated example of the neuromodulation device 202 includes a neuromodulation output circuit 204, a neuromodulation control circuit 206 with a processor 208, and a memory 210 with a neuromodulation parameter set 212. The neuromodulation device 202 can include other components, such as sensing circuitry for patient monitoring or feedback control of the therapy, telemetry circuitry, or power. The neuromodulation output circuit 204 is configured to produce and deliver neuromodulation pulses. The neuromodulation control circuit 206 is configured to control the delivery of the neuromodulation pulses using one or more neuromodulation parameters of the neuromodulation parameter set 212. In various examples, the neuromodulation control circuit 206 is configured to receive the one or more biomarker parameters from the one or more biomarker sensors 110 and control the neuromodulation pulses using the one or more biomarker parameters. For example, the processor 208 can be configured to adjust one or more parameters of the neuromodulation parameter set 212 in response to a change in the one or more biomarker parameters.

The lead system 214 can include one or more leads each configured to be electrically connected to the neuromodulation device 202. The lead system 214 can include a plurality of electrodes 216-1 to 216-N (where N≥2) distributed in an electrode arrangement using the one or more leads. Each lead can have an electrode array consisting of two or more electrodes, which also can be referred to as contacts. Multiple leads can provide multiple electrode arrays to provide the electrode arrangement. Each electrode in a single electrically conductive contact providing for an electrical interface between the neuromodulation output circuit 204 and tissue of the patient (e.g., the tissue site, or neural target). The neuromodulation pulses are each delivered from the neuromodulation output circuit 204 through a set of electrodes selected from the electrodes 216-1 to 216-N. The number of leads and the number of electrodes on each lead may depend on, for example, the distribution of targets of the neuromodulation and the need for controlling the distribution of electric field at each target. In an example, the lead system 214 can include two leads each having eight electrodes.

The neuromodulation system 100 can be configured to modulate spinal target tissue, brain tissue, or other neural tissue. For example, the neuromodulation system 100 can be configured to modulate neural activities at a tissue site such as in a dorsal column, a thalamus, a cortex, a peripheral nerve, a dorsal respiratory group, a dorsal longitudinal fasciculus, a dorsal horn, a vagus nerve, or a periaqueductal grey. The configuration of electrodes used to deliver electrical pulses to the tissue site (or another location associated with the neural activities at the tissue site) constitutes an electrode configuration, with the electrodes capable of being selectively programmed to act as anodes (positive), cathodes (negative), or left off (zero). In other words, an electrode configuration can represent the polarity being positive, negative, or zero. The neuromodulation parameter set includes parameters specifying the electrode configuration. Other parameters of the neuromodulation parameter set include, for example, the amplitude, pulse width, and rate (or frequency) of the electrical pulses. Each neuromodulation parameter set, including fractionalized current distribution to the electrodes (as percentage cathodic current, percentage anodic current, or off), may be stored, such as using the memory 210, and combined into a neuromodulation program that can then be used to modulate the tissue site or multiple regions within the patient.

The number of electrodes available combined with the ability to generate a variety of complex electrical pulses, presents a huge selection of neuromodulation parameter sets to the clinician or patient. For example, if the neuromodulation system to be programmed has sixteen electrodes, millions of modulation parameter sets may be available for programming into the neuromodulation system. Furthermore, for example SCS systems may have thirty-two electrodes which exponentially increases the number of modulation parameters sets available for programming. To facilitate such selection, the clinician generally programs the modulation parameters sets through a computerized programming system to allow more desirable modulation parameters to be determined based on patient feedback or other means and to subsequently program the desired modulation parameter sets.

Figure 3:
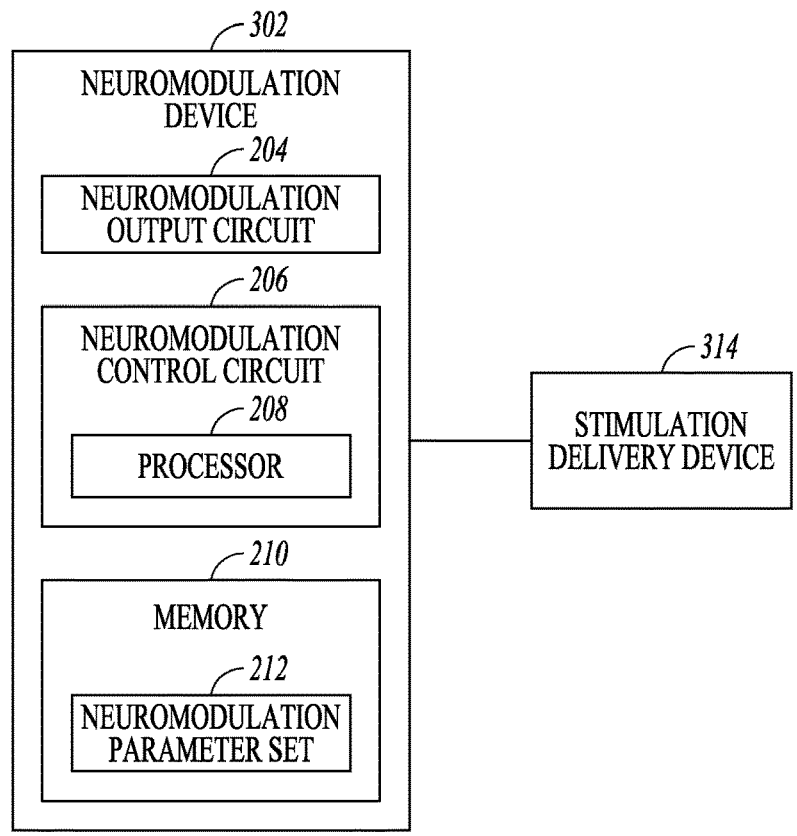
FIG. 3 illustrates an example of a neuromodulation device and a stimulation delivery device of a neuromodulation system, such as the system of FIG. 1.

FIG. 3 illustrates an example of a neuromodulation device 302, such as can be implemented as the neuromodulation device 104 in the neuromodulation system 100 of FIG. 1. In this example, the neuromodulation device 302 can be coupled to a stimulation delivery device 314. Stimulation delivery device 314 provides for an interface between neuromodulation device and the tissue site and produces stimuli capable of modulating neural activities and/or nervous tissue properties at the tissue site. Lead system 214 including electrodes 216 is one example of stimulation delivery device 314 when electrical stimuli are used for the neuromodulation. In various examples, stimulation delivery device 314 can be configured to deliver electrical, magnetic, optical, acoustic, chemical, pharmacological, and/or any other forms of stimuli.

In one example, neuromodulation energy may be delivered in the form of optical stimulation, in addition to or in place of the electrode stimulation. Stimulation delivery device 314 includes one or more light emitters to deliver optical stimuli for the neuromodulation. For example, infrared (IR) or near-IR energy deposition can be delivered to the tissue site, such as to provide anti-inflammatory effects. In one example, the one or more light emitters is configured to apply near-IR energy to the tissue site (e.g., the spinal cord or a brain target), such as to reduce inflammation and promote neuro-proliferation and neuro-regeneration.

In various examples, neuromodulation energy can be delivered in the form of electrical stimulation, magnetic stimulation, optical stimulation, acoustic stimulation, chemical or pharmacological stimulation, or a combination of two or more of such stimulations. Stimulation delivery device 314 can include one or more of lead and/or electrodes such as lead system 214 to deliver electrical stimuli such as electrical pulses, one or more electromagnets to deliver magnetic stimuli, one or more light emitters to deliver optical stimuli such as in the form of IR or near-IR energy, one or more acoustic energy emitters to deliver acoustic stimuli such as in the form of ultrasonic energy, and one or more drug delivery devices to deliver one or more chemical or pharmacological therapy agents. In an example, the neuromodulation output circuit 204 is configured to control delivery of stimulation from stimulation delivery device 314. In various examples, the present subject matter can be used to treat demyelinating, neurodegenerative, or neuroinflammatory diseases (e.g., such as multiple sclerosis, amyotrophic lateral sclerosis, Alzheimer's, depression, chronic pain, central pain, or fibromyalgia). neuromodulation.

The present subject matter can include determining an optimal tissue site for delivering the neuromodulation to treat a particular disease. In one example, the neuromodulation device (e.g., 104, 202, or 302) uses a quantitative measure of neuroinflammation at a tissue site to screen for an optimal stimulation target. The quantitative measure used can also be referred to as the biomarker parameter (which can be measure of a biomarker or a measure of a derivative of the biomarker) for the tissue site. By way of example, the biomarker can be a concentration of TSPO, temporal or spatial activation of microglial cells (also referred to as microglia), or a cytokine concentration in one or more particular tissue sites. In one example, the measure of the biomarker can be a quantification of microglial cell activation, such as can be associated with an amount of neuroinflammation in the dorsal horn or another tissue site. In one example, the biomarker parameter can be a cytokine concentration in the CSF, dorsal horn, brain ventricles, or another brain tissue. In one example, the biomarker parameter can be a quantification of TSPO levels in the dorsal horn, CSF, brain tissue, brain ventricles, the DRG, or another tissue site.

In one example, the biomarker parameter is a spatial measure that can be used to determine a spatial parameter used to control the delivery of neuromodulation. The spatial measure can be indicative of a spatial distribution of the biomarker for the tissue site. In an example, the biomarker parameter is a temporal measure that can be used to determine a temporal parameter used to control the delivery of the neuromodulation. The temporal measurement can be indicative of a change in the biomarker over time for the tissue site. The parameter can include a spatiotemporal parameter, such as can be determined using the spatial measurement and the temporal measurement of the biomarker.

In an example, the biomarker can be a metabolic biomarker. In this example, the biomarker parameter can be a measure of metabolism of the patient at a particular tissue site through quantification of ATP or a derivative (e.g., ADP, oxygen consumption, lactate, or pyruvate). For a neuroinflammatory condition, spatially-averaged cellular metabolic demand can increase relative to metabolic demand of a non-affected sites. The neuromodulation device can use the measure of the metabolism as the biomarker parameter, such as to determine a locus (e.g., center or region of high concentration) of neuroinflammation. A potential advantage of the present subject matter can include using the biomarker parameter to optimize neuromodulation targeting.

The present subject matter can include using the biomarker parameter to inform a treatment for the patient, such as an intervention that alleviates oxidative stress conditions (e.g., increasing the clearance of instigators of neuroinflammation, such as inflammatory cytokines through increase in blood flow). In an example, the treatment can be delivering neuromodulation to the inflamed tissue site. Such neuromodulation can be electrical or optical in nature. In an example, the neuromodulation is delivered to the tissue site. In an example, the neuromodulation is delivered via an upstream or downstream pathway (e.g., a descending inhibitory pathway involving the PAG or the DLF). In example, the neuromodulation is delivered to a tissue site that modulates inflammation systemically, such as to a site in the vagus nerve.

In one example, the biomarker can be measured using a sensor, which can be an implantable or external sensing system. In one example, the biomarker can be measured using an imaging system, such as a PET/MRI scanner, or other imaging modality. In this example, a radioligand can be used (e.g., a TSPO radioligand such as C-PBR28, C-(R)-PK11195, or PBR28). In various examples, the one or more biomarker sensors 110 represent such implantable or external sensing system or imaging system. The neuromodulation control circuit 206 can be configured to receive one or more biomarker parameters from the one or more biomarker sensors 110 and control the delivery of the neuromodulation using the one or more biomarker parameters. For example, the processor 208 can be configured to adjust one or more parameters of the neuromodulation parameter set 212 in response to a change in the one or more biomarker parameters. The neuromodulation parameter set 212 defines the waveform of stimuli used in the neuromodulation, such as electrical, magnetic, optical, acoustic, chemical, pharmacological, and/or any other forms of stimuli.

Figure 4:
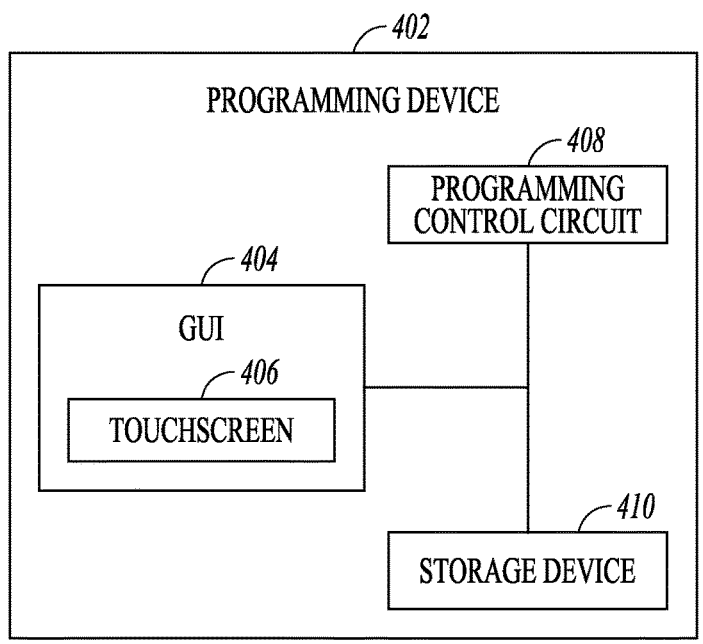
FIG. 4 illustrates an example of a programming device of a neuromodulation system, such as the system of FIG. 1.

FIG. 4 illustrates an example of a programming device 402, such as can be implemented as the programming device 102 in the neuromodulation system 100. The programming device 402 can include a memory or storage device 410 that can be referred to as storage, a programming control circuit 408, and a GUI 404. In the illustrated example, the GUI 404 includes a touchscreen 406. The programming control circuit 408 can be used to generate the neuromodulation parameter set (e.g., 212) that controls the delivery of the neuromodulation. In various examples, the GUI 404 can include any type of presentation device, such as interactive or non-interactive screens, and any type of user input devices that allow the user to program the user-programmable parameters of the neuromodulation parameter set, such as touchscreen, keyboard, keypad, touchpad, trackball, joystick, and mouse. The storage device 410 can store, among other things, the neuromodulation parameter set to be programmed into the neuromodulation device (e.g., 102, 202, or 302). The programming device 402 can transmit parameters of the neuromodulation parameter set to the neuromodulation device (e.g., 104, 202, or 302). In some examples, the programming device 402 can also transmit power to the neuromodulation device (e.g., 104, 202, or 302). The programming control circuit 408 can generate parameters of the neuromodulation parameter set. In various examples, the programming control circuit 408 may check values of certain parameters of the neuromodulation parameter set against safety rules to limit these values within constraints of the safety rules.

In some example, the neuromodulation control circuit 206 is configured to receive one or more biomarker parameters from the one or more biomarker sensors 110 and control the delivery of the neuromodulation using the one or more biomarker parameters, as discussed above. For example, programming device 402 can program the neuromodulation parameter set 212 into memory 210, and the neuromodulation control circuit 206 can adjust one or more parameters of the neuromodulation parameter set 212 in response to a change in the one or more biomarker parameters. In some other examples, the programming device 402 can be configured to receive one or more biomarker parameters sensed by the one or more biomarker sensors 110 and transmitted from the neuromodulation device (e.g., 104, 202, or 302), and the programming control circuit 408 can be configured to adjust one or more parameters of the neuromodulation parameter set using the one or more biomarker parameters. For example, the programming control circuit 408 can be configured to adjust one or more parameters of the neuromodulation parameter set 212 in response to a change in the one or more biomarker parameters. This is useful when, for example, the user (physician or other caregiver) is involved in adjusting the neuromodulation parameter set using the one or more biomarker parameters.

In various examples, circuits of the neuromodulation system 100, including its various examples discussed in this document, may be implemented using a combination of hardware, software and firmware. For example, the circuit of the GUI 404, the neuromodulation control circuit 206, and the programming control circuit 408 may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 5:
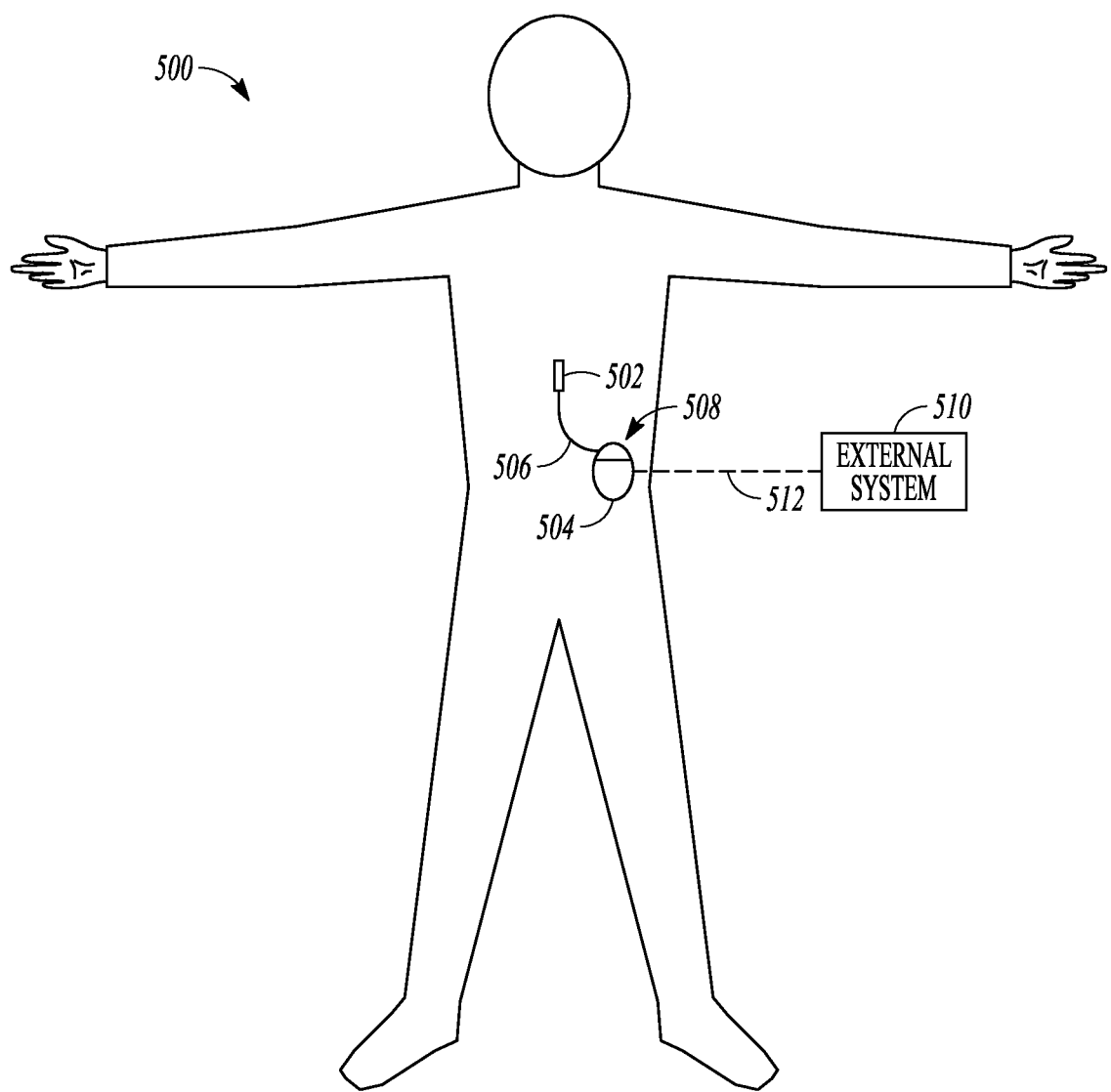
FIG. 5 illustrate an example of an implantable neuromodulation system and portions of an environment in which the system may be used.

FIG. 5 illustrates an example of an implantable neuromodulation system 500 and portions of an environment in which the system 500 may be used. The system 500 is illustrated by way of example, but not by way of limitation, as being implanted near the spinal cord of a patient. In various examples, the system 500 can be configured to be implanted in various locations in the patient to modulate various neural targets, such as the tissue sites for modulating neuroinflammation as discussed in this document. The system 500 can include an implantable system 508, an external system 510, and a telemetry link 512 providing for wireless communication between the implantable system 508 and the external system 510. The implantable system 508, illustrated as being implanted in the patient's body, includes an implantable neuromodulation device (also referred to as an implantable pulse generator, or IPG) 504, a lead system 506, and electrodes 502. In various examples, the neuromodulation device 104, 202, or 302 can be implemented as the implantable neuromodulation device 504, the lead system 214 can be implemented as the lead system 506, and the electrodes 106 or 214 can be implemented as the electrodes 502. The lead system 506 includes one or more leads each configured to be electrically connected to the implantable neuromodulation device 504 and a plurality of electrodes 502 distributed in the one or more leads. In various examples, the external system 510 includes one or more external (non-implantable) devices each allowing a user (e.g. a clinician or other caregiver and/or the patient) to communicate with the implantable neuromodulation device 504. In various examples, the programming device 402 can be implemented as such an external device. In some examples, the external system 510 includes a programming device intended for a clinician or other caregiver to initialize and adjust settings for the implantable neuromodulation device 504 and a remote control device intended for use by the patient. For example, the remote control device may allow the patient to turn a therapy on and off and/or adjust certain patient-programmable parameters of the plurality of modulation parameters.

The neuromodulation lead(s) of the lead system 506 may be placed adjacent, e.g., resting near, or upon the dura, adjacent to the spinal cord area to be stimulated. For example, the neuromodulation lead(s) may be implanted along a longitudinal axis of the spinal cord of the patient. Due to the lack of space near the location where the neuromodulation lead(s) exit the spinal column, the implantable modulation FIG. 6 illustrates an example of some features of the neuromodulation leads 604 and a neuromodulation device 602. The neuromodulation device 602 may be an implantable device or may be an external. In the illustrated example, one of the neuromodulation leads has eight electrodes (labeled E1-E8), and the other neuromodulation lead has eight electrodes (labeled E9-E16). The actual number and shape of leads and electrodes may vary for the intended application. An implantable device may include an outer case for housing the electronic and other components. The outer case may be composed of an electrically conductive, biocompatible material, such as titanium, that forms a hermetically-sealed compartment wherein the internal electronics are protected from the body tissue and fluids. In some cases, the outer case may serve as an electrode (e.g. case electrode).

The implanted device may include electronic components, such as a controller/processor (e.g., a microcontroller), memory, a battery, telemetry circuitry, monitoring circuitry, modulation output circuitry, and other suitable components known to those skilled in the art. The microcontroller executes a suitable program stored in memory, for directing and controlling the neuromodulation performed by the implanted device.

Electrical neuromodulation energy is provided to the electrodes in accordance with the neuromodulation parameter set programmed into the neuromodulation device. The neuromodulation energy may be in the form of a pulsed electrical waveform. Such neuromodulation parameters may comprise electrode combinations, which define the electrodes that are activated as anodes (positive), cathodes (negative), and turned off (zero), percentage of neuromodulation energy assigned to each electrode (fractionalized electrode configurations), and electrical pulse parameters, which define the pulse amplitude (measured in milliamps or volts depending on whether the pulse generator supplies constant current or constant voltage to the electrode array), pulse width (measured in microseconds), pulse rate (measured in pulses per second), and burst rate (measured as the modulation on duration X and modulation off duration Y). The electrical pulse parameters may define an intermittent neuromodulation with "on" periods of time where a train of two or more pulses are delivered and "off" periods of time where pulses are not delivered. Electrodes that are selected to transmit or receive electrical energy are referred to herein as "activated," while electrodes that are not selected to transmit or receive electrical energy are referred to herein as "non-activated."

Electrical neuromodulation occurs between or among a plurality of activated electrodes, one of which may be a case electrode of the implanted device. The system may be capable of transmitting neuromodulation energy to the tissue in a monopolar or multipolar (e.g., bipolar, tripolar, etc.) fashion. Monopolar neuromodulation occurs when a selected one of the lead electrodes is activated along with the case of the neuromodulation device, so that neuromodulation energy is transmitted between the selected electrode and case.

Any of the electrodes (e.g. E1-E16 and the case electrode) may be assigned to up to k possible groups or timing "channels." In one example, k may equal four. The timing channel identifies which electrodes are selected to synchronously source or sink current to create an electric field in the tissue to be stimulated. Amplitudes and polarities of electrodes on a channel may vary. In particular, the electrodes can be selected to be positive (anode, sourcing current), negative (cathode, sinking current), or off (no current) polarity in any of the k timing channels.

The neuromodulation device may be configured to individually control the magnitude of electrical current flowing through each of the electrodes, which may be referred to as multiple independent current control (MICC). For example, a current generator may be configured to selectively generate individual current-regulated amplitudes from independent current sources for each electrode. In some examples, the pulse generator may have voltage regulated outputs. While individually programmable electrode amplitudes are desirable to achieve fine control, a single output source switched across electrodes may also be used, although with less fine control in programming. The neuromodulation device may be designed with mixed current and voltage regulated devices. The individual control of electrical current through each of the electrodes allows the neuromodulation device to fractionalize the current. The fractionalization across the neuromodulation lead can vary in any manner as long as the total of fractionalized currents equals 100%.

The SCS system may be configured to deliver different electrical fields to achieve a temporal summation of modulation. The electrical fields can be generated respectively on a pulse-by-pulse basis. For example, a first electrical field can be generated by the electrodes (using a first current fractionalization) during a first electrical pulse of the pulsed waveform, a second different electrical field can be generated by the electrodes (using a second different current fractionalization) during a second electrical pulse of the pulsed waveform, a third different electrical field can be generated by the electrodes (using a third different current fractionalization) during a third electrical pulse of the pulsed waveform, a fourth different electrical field can be generated by the electrodes (using a fourth different current fractionalized) during a fourth electrical pulse of the pulsed waveform, and so forth. These electrical fields may be rotated or cycled through multiple times under a timing scheme, where each field is implemented using a timing channel. The electrical fields may be generated at a continuous pulse rate, or as bursts of pulses. Furthermore, the interpulse interval (i.e., the time between adjacent pulses), pulse amplitude, and pulse duration during the electrical field cycles may be uniform or may vary within the electrical field cycle. Various examples stochastically modulate values for one or more neuromodulation parameters such as these and others.

Some examples are configured to provide a neuromodulation parameter set to create a desired neuromodulation field shape (e.g. a broad and uniform neuromodulation field such as may be useful to prime targeted neural tissue with sub-perception modulation or a field shape to reduce or minimize modulation of non-targeted tissue. Various examples stochastically modulate values of one or more neuromodulation parameters associated with controlling the field shape in order to stochastically modulate the neuromodulation field shape.

FIG. 7A illustrates a schematic view of an example of a single neuromodulation lead 704 implanted over approximately the longitudinal midline of the patient's spinal cord 702.

FIG. 7B illustrates a schematic view of an example of an neuromodulation lead 708 that has been implanted more laterally with respect to the spinal cord 706, thereby placing it proximate the dorsal horn (DH) of the spinal cord, and the other neuromodulation lead 710 that has been implanted more medially with respect to the spinal cord, thereby placing it proximate the dorsal column (DC) of the spinal cord 706.

It is understood that additional leads or lead paddle(s) may be used, such as may be used to provide a wider electrode arrangement and/or to provide the electrodes closer to dorsal horn elements, and that these electrode arrays also may implement fractionalized current. Placement of the lead more proximate to the DH than the DC may be desirable to preferentially stimulate DH elements over DC neural elements for a subperception therapy. Lead placement may also enable preferential modulation of dorsal roots over other neural elements. Any other plurality of leads or a multiple column paddle lead can also be used. Longitudinal component of the electrical field is directed along the y-axis depicted in FIG. 7A, and a transverse component of the electrical field is directed along the x-axis depicted in FIG. 7A.

Figure 8:
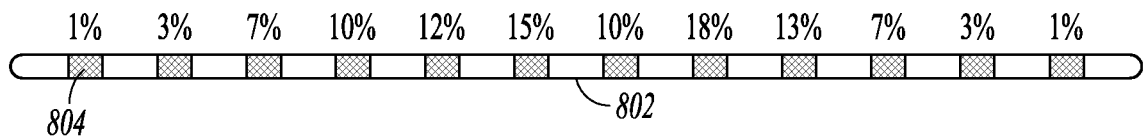
FIG. 8 illustrates a schematic view of an example of the neuromodulation lead showing an example of the fractionalization of the anodic current delivered to the electrodes on the neuromodulation lead.

FIG. 8 illustrates a schematic view of an example of the neuromodulation lead 802 showing an example of the fractionalization of the anodic current delivered to the electrodes on the neuromodulation lead. This figure illustrates fractionalization using monopolar modulation where a case electrode of the IPG is the only cathode, and carries 100% of the cathodic current. The fractionalization of the anodic current shown in FIG. 8 does not deliver an equal amount of current to each electrode 804, because this example takes into account electrode/tissue coupling differences, which are the differences in how the tissue underlying each electrode reacts to neuromodulation. Also, the ends of the portion of the neuromodulation lead include electrodes having lower gradient in the longitudinal direction. The magnitude of the electrical field tapers down at the ends of the neuromodulation lead. Fractionalization of the current may accommodate variation in the tissue underlying those electrodes. The fractionalization across the neuromodulation lead can vary in any manner as long as the total of fractionalized currents equals 100%. Various examples described herein implement a programmed algorithm to determine the appropriate fractionalization to achieve a desired modulation field property.

Modulation thresholds vary from patient to patient and from electrode to electrode within a patient. An electrode/tissue coupling calibration of the electrodes may be performed to account for these different modulation thresholds and provide a more accurate fractionalization of the current between electrodes. For example, perception threshold may be used to normalize the electrodes. The RC or the CP may be configured to prompt the patient to actuate a control element, once paresthesia is perceived by the patient. In response to this user input, the RC or the CP may be configured to respond to this user input by storing the modulation signal strength of the electrical pulse train delivered when the control element is actuated. Other sensed parameter or patient-perceived modulation values (e.g. constant paresthesia, or maximum tolerable paresthesia) may be used to provide the electrode/tissue coupling calibration of the electrodes.

The SCS system may be configured to deliver different electrical fields to achieve a temporal summation of modulation. The electrical fields can be generated respectively on a pulse-by-pulse basis. For example, a first electrical field can be generated by the electrodes (using a first current fractionalization) during a first electrical pulse of the pulsed waveform, a second different electrical field can be generated by the electrodes (using a second different current fractionalization) during a second electrical pulse of the pulsed waveform, a third different electrical field can be generated by the electrodes (using a third different current fractionalization) during a third electrical pulse of the pulsed waveform, a fourth different electrical field can be generated by the electrodes (using a fourth different current fractionalized) during a fourth electrical pulse of the pulsed waveform, and so forth. These electrical fields can be rotated or cycled through multiple times under a timing scheme, where each field is implemented using a timing channel. The electrical fields may be generated at a continuous pulse rate, or as bursts of pulses. Furthermore, the interpulse interval (i.e., the time between adjacent pulses), pulse amplitude, and pulse duration during the electrical field cycles may be uniform or may vary within the electrical field cycle. Some examples are configured to determine a modulation parameter set to create a field shape to provide a broad and uniform modulation field such as may be useful to prime targeted neural tissue with sub-perception modulation. Some examples are configured to determine a modulation parameter set to create a field shape to reduce or minimize modulation of non-targeted tissue (e.g., dorsal column tissue). Various examples disclosed herein are directed to shaping the modulation field to enhance modulation of some neural structures and diminish modulation at other neural structures. The modulation field may be shaped by using multiple independent current control (MICC) or multiple independent voltage control to guide the estimate of current fractionalization among multiple electrodes and estimate a total amplitude that provide a desired strength. For example, the modulation field may be shaped to enhance the modulation of dorsal horn neural tissue and to minimize the modulation of dorsal column tissue. A benefit of MICC is that MICC accounts for various in electrode-tissue coupling efficiency and perception threshold at each individual contact, so that "hotspot" stimulation is eliminated.

Figure 9:
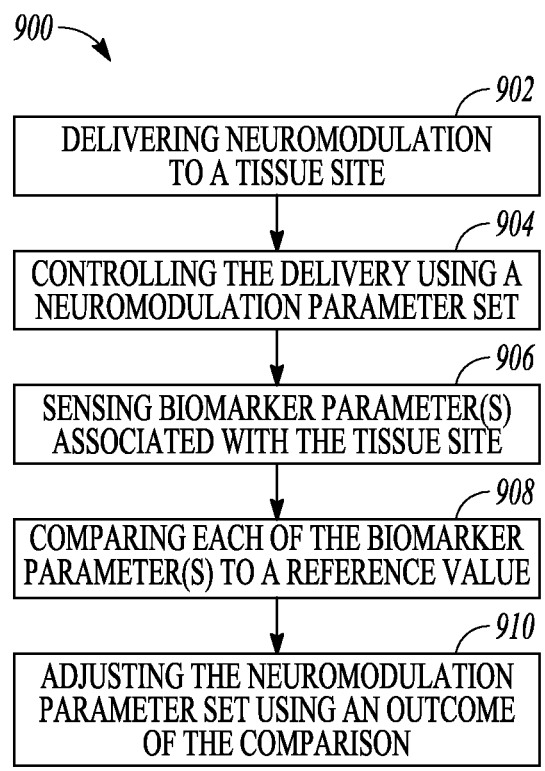
FIG. 9 illustrates an example of a method for delivering neuromodulation.

FIG. 9 illustrates an example of a method 900 of delivering neuromodulation. In various examples, the neuromodulation system 100 can be configured to perform the method 900. In various examples, an implantable neuromodulation system (e.g., 500) can be configured to perform the method 900.

At 902, neuromodulation is delivered to a tissue site or another location that is associated with neural activities at the tissue site, such as from the neuromodulation device 104, 202, or 302. Examples of the tissue site include the tissue site for modulating neuroinflammation as discussed in this document.

At 904, the delivery of neuromodulation to the tissue site is controlled using a neuromodulation parameter set. The neuromodulation parameter set can include a plurality of neuromodulation parameters that can be temporal or spatial parameters defining a pattern according to which the neuromodulation energy is delivered, such as a waveform including a plurality of electrical pulses.

At 906, one or more biomarker parameters associated with the tissue site are sensed using one or more biomarker sensors (e.g., 110). The one or more biomarker parameters each indicate a neural or other physiological response to the delivery of the neuromodulation. The one or more biomarkers are each a measure of the biomarker or a measure of a derivative of the biomarker. In one example, the one or more sensed biomarker parameters are stored, such as in the memory 210.

At 908, one or more biomarker parameters are each compared to a reference value, such as by using the processor 208. In an example, the reference value or value range can be a stored value in the memory 210. In one example, the reference value or value range can be a previously sensed value of the corresponding biomarker parameter. In an example, the reference value can be determined from clinical data, such as obtained during a clinical trial.

At 910, the neuromodulation parameter set are adjusted using an outcome of the comparison. In one example, the reference value or value range represents a threshold indicative of a need for treating neuroinflammation, and the outcome of the comparison indicates such a need. In one example, the reference value or value range represents a degree of neuroinflammation, and the outcome of the comparison indicates an intensity of the neuromodulation needed for treating the neuroinflammation at the indicted degree.

A potential advantage of the present subject matter can include determining patient-specific therapies. The neuromodulation device can aid in determining that, for a first patient "A" with a modulation target "X", a spatiotemporal neuromodulation parameter set "Y" is optimal for patient "A". However, for example, the neuromodulation device can aid in determining that, for a second patient "B" with a modulation target "U," a spatiotemporal neuromodulation parameter set "W" is optimal for patient "B." In an example, the present subject matter can be used for therapies of single targets or for multiple targets, such as complex multimodal treatment paradigms (e.g., dorsal column stimulation with neuromodulation parameter set "C" with DRG stimulation with neuromodulation parameter set "D").

In some examples, the method 900, or variants of any part of the method 900, can be implemented as instructions stored in a machine readable storage medium. The machine can be in a form of a computer system, which can include a processor, memory, video display unit, an alpha-numeric input device, and a user interface with a navigation device, a disk drive unit, a signal generation device, a network interface device, among others. The instructions can cause machine to perform any part of the method 900 or any variants thereof. The instructions can also cause the machine for displaying an output.

The machine can operate as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a PDA, a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The machine-readable medium may include a single medium or multiple media (e.g., a centralized or distributed database, and/or associated caches and servers) that store the one or more instructions or data structures. The term "machine-readable storage medium" shall also be taken to include any tangible medium that is capable of storing, encoding or carrying instructions for execution by the machine and that cause the machine to perform any one or more of the methods of the present invention, or that is capable of storing, encoding or carrying data structures used by or associated with such instructions. The term "machine-readable storage medium" shall accordingly be taken to include, but not be limited to, solid-state memories, and optical and magnetic media. Specific examples of machine-readable media include non-volatile memory, including by way of example, semiconductor memory devices (e.g., erasable programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks. A "machine-readable storage medium" shall also include devices that may be interpreted as transitory, such as register memory, processor cache, and RANI, among others. The definitions provided herein of machine-readable medium and machine-readable storage medium are applicable even if the machine-readable medium is further characterized as being "non-transitory." For example, any addition of "non-transitory," such as non-transitory machine-readable storage medium, is intended to continue to encompass register memory, processor cache and RANI, among other memory devices.

In various examples, the instructions may further be transmitted or received over a communications network using a transmission medium. The instructions may be transmitted using the network interface device and any one of a number of well-known transfer protocols (e.g., HTTP). Examples of communication networks include a LAN, a WAN, the Internet, mobile telephone networks, plain old telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventors also contemplate examples in which only those elements shown or described are provided. Moreover, the present inventors also contemplate examples using combinations or permutations of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

What is claimed is:

1. A method for delivering neuromodulation energy to a patient having a spinal cord, the method comprising:
   delivering the neuromodulation energy from an implantable neuromodulation device to the spinal cord through one or more implantable electrodes placed over the spinal cord to modulate neuroinflammation in the patient;
   controlling the delivery of the neuromodulation energy using neuromodulation parameters using a control circuit of the implantable neuromodulation device;
   determining a measure of a biomarker of neuroinflammation or a derivative of the biomarker of neuroinflammation; and
   adjusting the neuromodulation parameters using the determined measure of the biomarker using the control circuit.

2. The method of claim 1, wherein determining the measure of the biomarker of neuroinflammation or the derivative of the biomarker of neuroinflammation comprises determining the measure of the biomarker of neuroinflammation or the derivative of the biomarker of neuroinflammation using an imaging system.

3. The method of claim 1, wherein determining the measure of the biomarker of neuroinflammation or the derivative of the biomarker of neuroinflammation comprises sensing one or more biomarker parameters using one or more sensors.

4. The method of claim 3, wherein sensing the one or more biomarker parameters comprises sensing a quantitative measure of neuroinflammation in the spinal cord.

5. The method of claim 3, further comprising:
   comparing the one or more biomarkers each to a reference value or value range; and
   adjusting the neuromodulation parameters using an outcome of the comparison.

6. The method of claim 5, wherein the reference value or value range represents a threshold indicative of a need for treating the neuroinflammation, and the outcome of the comparison indicates the need.

7. The method of claim 5, wherein the reference value or value range represents a degree of the neuroinflammation, and the outcome of the comparison indicates an intensity of the neurostimulation needed for treating the neuroinflammation at the indicated degree.

8. The method of claim 1, wherein determining the measure of the biomarker of neuroinflammation or the derivative of the biomarker of neuroinflammation comprises determining a quantification of microglial cell activation.

9. The method of claim 1, wherein determining the measure of the biomarker of neuroinflammation or the derivative of the biomarker of neuroinflammation comprises determining a cytokine concentration.

10. The method of claim 1, wherein determining the measure of the biomarker of neuroinflammation or the derivative of the biomarker of neuroinflammation comprises determining a quantification of translocator protein levels.

11. The method of claim 1, wherein determining the measure of the biomarker of neuroinflammation or the derivative of the biomarker of neuroinflammation comprises determining a spatial measure indicative of a spatial distribution of the biomarker.

12. The method of claim 1, wherein determining the measure of the biomarker of neuroinflammation or the derivative of the biomarker of neuroinflammation comprises determining a temporal measure indicative of a change in the biomarker over time.

13. The method of claim 1, wherein determining the measure of the biomarker of neuroinflammation or the derivative of the biomarker of neuroinflammation comprises determining a measure of metabolism.

14. A non-transitory computer-readable storage medium including instructions, which when executed by a system, cause the system to perform a method for delivering neuromodulation energy to a patient having a spinal cord, the method comprising:
   delivering the neuromodulation energy from an implantable neuromodulation device to the spinal cord through one or more implantable electrodes placed over the spinal cord to modulate neuroinflammation in the patient;
   controlling the delivery of the neuromodulation energy using neuromodulation parameters using a control circuit of the implantable neuromodulation device;
   determining a measure of a biomarker of neuroinflammation; and
   adjusting the neuromodulation parameters using the determined measure of the biomarker using the control circuit.

15. The non-transitory computer-readable storage medium of claim 14, wherein determining the measure of the biomarker of neuroinflammation or the derivative of the biomarker of neuroinflammation comprises sensing one or more biomarker parameters using one or more sensors.

16. The non-transitory computer-readable storage medium of claim 15, wherein sensing the one or more biomarker parameters comprises sensing a quantitative measure of neuroinflammation in the spinal cord.

17. A system for delivering neuromodulation energy to a patient having a spinal cord, the system comprising:
   one or more implantable electrodes configured to be placed over the spinal cord;
   a neuromodulation output circuit configured to be coupled to the one or more implantable electrodes and to deliver neuromodulation energy to the spinal cord through the one or more implantable electrodes; and
   a control circuit configured to control the delivery of the neuromodulation energy to the spinal cord to modulate neuroinflammation in the patient using neuromodulation parameters, to determining a measure of a biomarker of neuroinflammation, and to adjust the neuromodulation parameters using the determined measure of the biomarker.

18. The system of claim 17, further comprising a biomarker sensor configured to sense the biomarker parameter, wherein the biomarker sensor is configured to sense the biomarker parameter being a measure of at least one of a translocator protein concentration, a measure of a temporal activation of the microglial cell, a measure of a spatial activation of the microglial cell, or a measure of a cytokine concentration.

19. The system of claim 18, wherein the biomarker sensor is configured to sense a biomarker parameter indicative of an intensity of pain.

20. The system of claim 18, wherein the biomarker sensor is configured to sense a quantitative measure of neuroinflammation in the spinal cord.

* * * * *